United States Patent [19]

Ishimori et al.

[11] Patent Number: 4,761,054
[45] Date of Patent: Aug. 2, 1988

[54] INFRARED FIBER CABLE

[75] Inventors: Akira Ishimori; Takashi Yamamoto, both of Hyogo; Tsuyoshi Kinoshita, Nagasaki, all of Japan

[73] Assignee: Mitsubishi Denki Kabushiki Kaisha, Tokyo, Japan

[21] Appl. No.: 106,926

[22] Filed: Oct. 7, 1987

Related U.S. Application Data

[63] Continuation of Ser. No. 783,824, Oct. 3, 1985.

[30] Foreign Application Priority Data

Oct. 4, 1984 [JP]  Japan .................. 59-207010
May 27, 1985 [JP] Japan .................. 60-113475
Jun. 12, 1985 [JP] Japan .................. 60-126325

[51] Int. Cl.$^4$ .............................................. G02B 23/26
[52] U.S. Cl. ............................ 350/96.26; 350/96.18
[58] Field of Search ............ 350/96.10, 96.15, 96.18, 350/96.20, 96.23, 96.24, 96.26; 128/395

[56] References Cited

U.S. PATENT DOCUMENTS 4,170,997 10/1979 Pinnow et al. ............ 350/96.26 X
4,402,569  9/1983 Bow et al. ................... 350/96.26
4,458,683  7/1984 Saito et al. ..................... 128/395
4,500,181  2/1985 Takahashi .................. 350/96.26 X

FOREIGN PATENT DOCUMENTS 0116350 11/1983 Japan .

OTHER PUBLICATIONS

Ikedo, M., et al., "Infrared Optical Fiber for Energy Transmission", Studies on Laser, v. 11, n. 11, pp. 20-27, 1983.

Primary Examiner—Eugene R. LaRoche
Assistant Examiner—Steven J. Mottola
Attorney, Agent, or Firm—Wolf, Greenfield & Sacks

[57] ABSTRACT

An infrared fiber cable having a protective tube isolating the light for collimation which is a visible light. An infrared fiber is accommodated in the protective tube and adapted to conduct and emit an invisible light. Light emitting means is disposed around the infrared fiber and adapted to emit the light for collimation. The infrared fiber cable further includes a member adapted to allow the invisible light to pass therethrough but reflect the light for collimation. Also, an apparatus for preventing erroneous emission for a laser scalpel to be attached to such an optical fiber is provided. The apparatus operates to control emission of the laser beam for surgical operation in response to the position of the emission end of the optical fiber with respect to the object to be surgically operated.

17 Claims, 12 Drawing Sheets

Fig. 3
(PRIOR ART)
Fig. 4
(PRIOR ART)
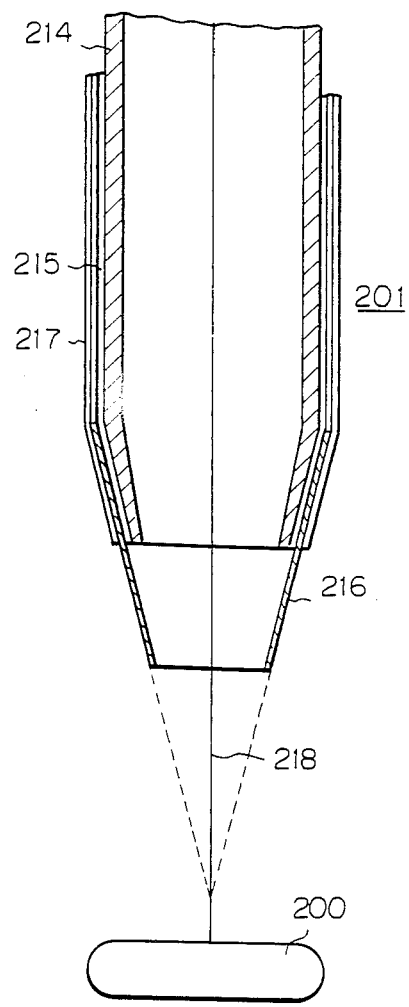
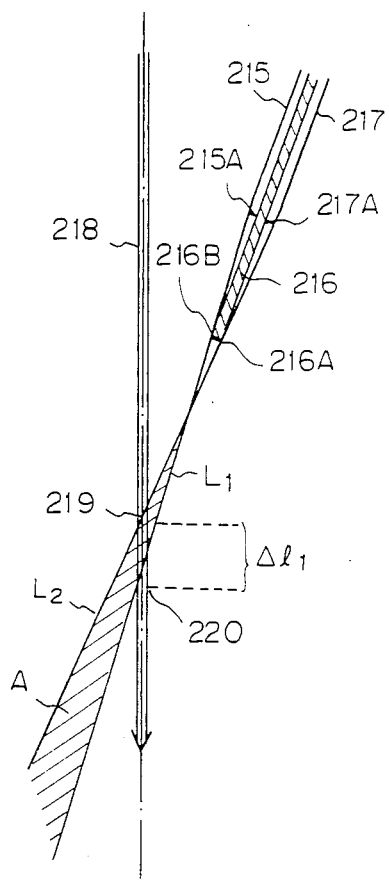

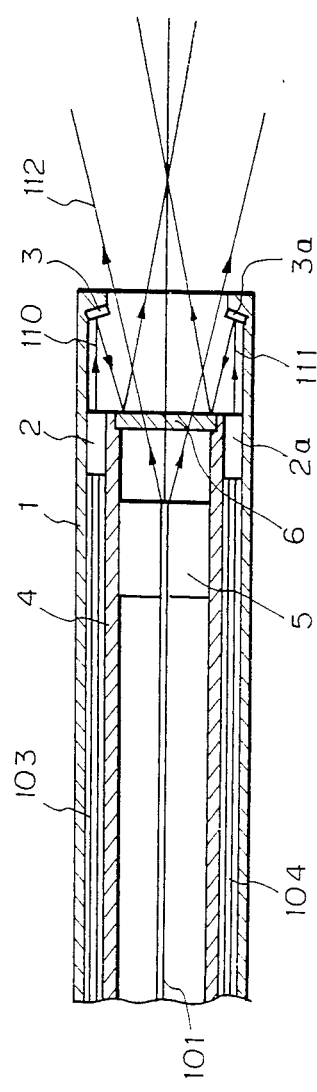
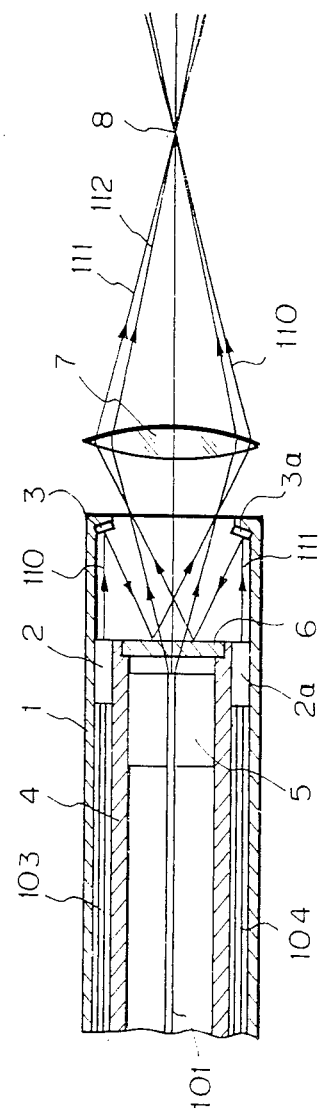
Fig. 6
Fig. 7

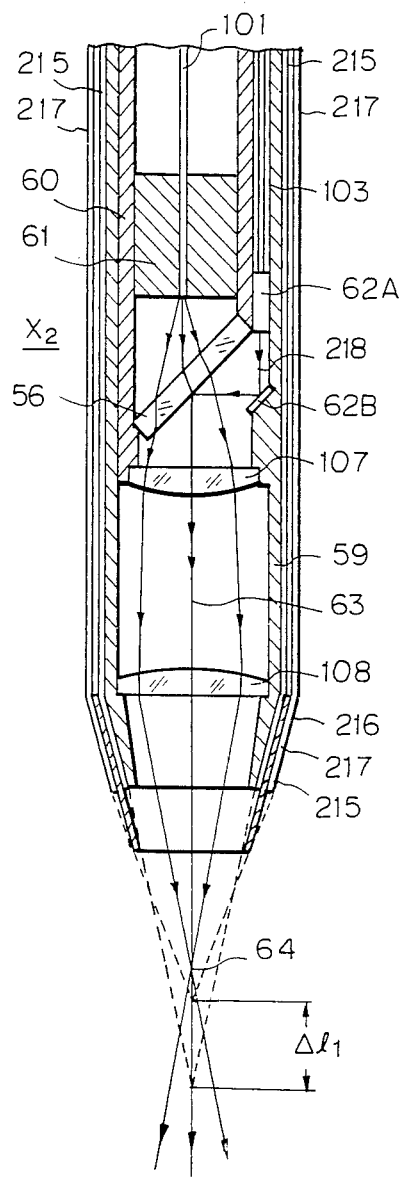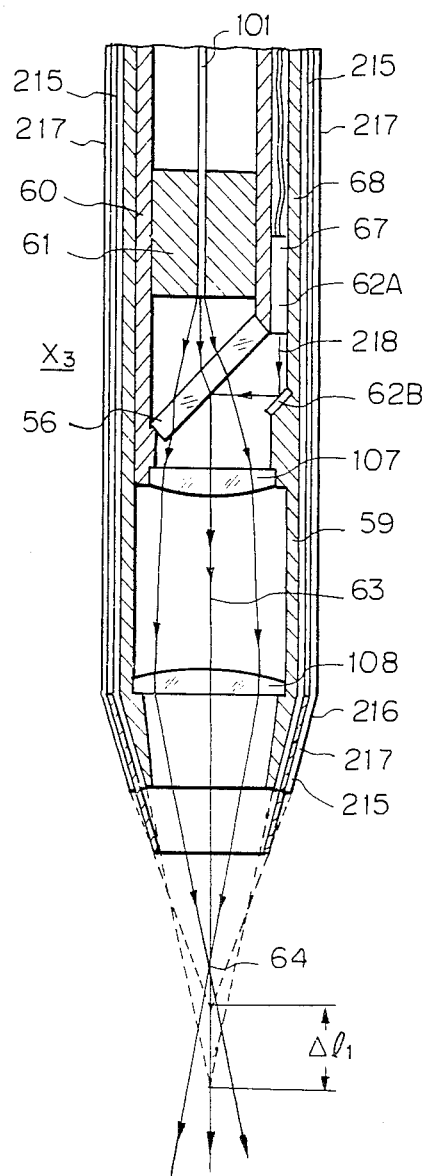

INFRARED FIBER CABLE

This application is a continuation of application Ser. No. 783,824, filed Oct. 3, 1985.

TECHNICAL FIELD OF THE INVENTION

The present invention relates to an infrared fiber cable and more particularly to the particular construction of the emission end of an infrared fiber cable as well as an apparatus for preventing erroneous emission of the laser which is mounted on such an infrared fiber cable and adapted to enable the laser to emit only when the position of the object to be irradiated with the laser is located within a predetermined value range.

BACKGROUND OF THE INVENTION

FIG. 1 illustrates a $CO_2$ laser scalpel of an optical fiber type as described in the article entitled "Infrared Optical Fiber for Energy Transmission" contributed by M. Ikedo et al. and printed in "Studies on Laser" No. 11, vol. 11 published on Nov. 30, 1983 by the Japanese Laser Institute. In case of $CO_2$ laser scalpel of an optical fiber type, since the infrared fiber which normally allows the infrared light such as $CO_2$ laser light or the like to be transmitted therethrough will not allow the visible light to pass therethrough, the laser light as the collimation light is introduced from the area around the circumference of the infrared fiber. In FIG. 1, numeral 101 designates the infrared fiber as above mentioned; numeral 102 the metallic tube which covers the area except the tip end portion of the infrared fiber 101; numerals 103 and 104 two optical fibers for the collimation light which serve to conduct the collimation light; numerals 105, 106 micro lenses which are respectively mounted at the emission ends of the optical fibers 103, 104 for the collimation light and condenses the collimation light so as to orient the collimation light to the optical axis of the infrared fiber 101; numeral 107 the first condensing lens which is provided in front of the infrared fiber 101 and the micro lenses 105, 106; numeral 108 the second condensing lens which is provided in front of the first condensing lens 107; and numeral 109 a hollow outer tube which supports the infrared fiber 101 at the portion adjacent to the emission end thereof by way of a metallic tube 102, supports the output end of the optical fibers 103 and 104 for the collimation light as well as the micro lenses 105 and 106 and supports both condensing lenses 107 and 108 so that the optical axis of the condensing lenses 107 and 108 may collide with the axis of the infrared fiber 101. Further, the condensing lenses 107 and 108 and other elements are so arranged that the laser light 110 and 111 for collimation emitted from the micro lenses 105 and 106 and the laser light 112 for surgical operation purposes emitted from the infrared fiber 101 are focused at the identical spot 113 formed in front of the second condensing lens 108 by way of the first and second condensing lenses 107 and 108.

In the conventional infrared fiber cable constructed as above mentioned, when the collimation beam lights 110, 111 are emitted through the micro lenses 105, 106, these collimation light beams 110, 111 pass over the location adjacent to the tip end portion of the infrared fiber 101. As the result, there has been such a problem as the infrared fiber 101 which is photosensitive would be markedly deteriorated. On the other hand, it may be also conceived that the collimation light beams 110, 111 are caused to emit from the outside of the emission end casing 109 in order to prevent the infrared fiber 101 from being deteriorated. However, this concept has caused such a problem as to degrade maneuvability of the emission end of the infrared fiber. Further, the laser beam for collimation must pass through the center of the emission end of the laser. Moreover, in case of the $CO_2$ laser scalpel of optical fiber type, an infrared fiber is usually used. However, the infrared fiber will not allow the visible light to pass therethrough, and consequently it often happens that the collimation light is introduced around the circumference of the infrared fiber. In this sort of construction, there has been such a problem as an apparatus for preventing erroneous emission cannot be incorporated. The detailed description will follow in this respect.

FIG. 2 is a schematic illustration of the erroneous emission preventive apparatus for a laser scalpel provided with an optical path of a conventional multi-articulation mirror manipulator type (refer to the Japanese Patent Public Disclosure Gazette No. 116350/83). In FIG. 2, numeral 200 designates the object to be surgically operated; numeral 201 the emission end for the laser light provided at the tip end of the laser scalpel adapted to apply the laser to the object 200 to be surgically operated by emitting both visible laser light for collimation and the invisible laser light for surgical operation; numerals 202 and 203 light detectors disposed at the position to receive the output light from the respective inner layer and outer layer optical fibers to be described later which are secured to the laser emission end 201 adapted to receive and conduct the collimation laser light reflected by the object 200 to be surgically operated; numerals 204 and 205 preamplifiers the inputs of which are connected respectively to the outputs of said light detectors 202, 203 and are adapted to amplify the output signals from these light detectors; numeral 206 a differential amplifier adapted to amplify the difference of the outputs between the preamplifier 204 and the preamplifier 205; numeral 207 a lock-in amplifier adapted to provide the DC approximated signal by receiving the AC output signals from the differential amplifier 206 and approximating them by excluding the differential component due to noise signal affected by the external light in accordance with the phase of the modulated signal received from the optical chopper portion 213 to be described; numeral 208 a comparator adapted to compare the output of the lock-in amplifier 207 with the reference value (OV for example in the present embodiment) and thus determine the irradiated position of the object 200 to be surgically operated; numeral 209 a laser control part adapted to control the output of the laser light for surgical operation by receiving the signal determining the irradiated position provided by said comparator 209; numeral 210 a power supply source for the laser light for surgical operation output of which is controlled by the laser control part 209; numeral 211 an oscillation tube part for the laser light for surgical operation adapted to generate the laser light for surgical operation by receiving the output of the laser supply power source 210; numeral 212 the laser supply source for the collimation light having a power source incorporated therein and adapted to generate the collimation laser light by the oscillation tube; and numeral 213 an optical chopper part adapted to optically modulate by means of a modulated signal the collimation laser light provided by the laser supply source 212 for the collimation light so as to separate the collimation light from the external light. It is to be noted that the laser light for collimation provided by the optical chopper part 213 and the laser light for surgical operation provided by the oscillation tube part for generating the laser for surgical operation are both conducted by the multi-articulation mirror of a known laser scalpel of multi-articulation mirror type and the optical axis of both laser lights are combined so that they are directed to the emission end 201 for the laser lights.

FIG. 3 is the vertical sectional view of the laser light emission end 201 shown in FIG. 2 wherein numeral 214 designates a hollow cylindrical body which is cylindrical in the configuration, the tip end portion thereof is inclined toward the central axis and also the tip end of which is provided with a circular opening; numeral 215 a multiplicity of inner layer optical fibers of which tip end portions are provided along the outer wall of said hollow cylindrical body 214 and which are disposed in a manner that a multiplicity of circular lateral sectional portions of said inner layer optical fibers surround the periphery of the annular sectional portion of said hollow cylindrical member 214; numeral 216 an orientation cylinder member having a constant wall thickness which is so provided as to surround the circumference of said inner layer optical fibers 215 at the inclined portion of said hollow cylindrical body 214, and has a similar configuration to said inclined portion of the hollow cylindrical body 214 as well as an opening still ahead of the opening of said hollow cylindrical body 214; numeral 217 a multiplicity of outer layer optical fibers the tip end portions of which are disposed along the outer wall of said orientation cylinder 216 concentrically with said inner layer optical fibers 215; and numeral 218 the laser light for collimation emitted in alignment with the central axis of said orientation cylinder 216. Further, it is to be noted that the input ends of the inner layer optical fiber 215 and the outer layer optical fiber 217 are located substantially on the surface of the opening of the hollow cylindrical body 214 and inclined relative to the laser light 218 for collimation. It is also to be noted that the light detectors 202 and 203 as shown in FIG. 2 are provided respectively at the output ends of the inner layer optical fibers 215 and outer layer optical fibers 217.

Operation of the illustrated apparatus will now be explained. The laser light for collimation generated by the laser supply source 212 for the collimation laser light is converted into the intermittent light by means of the optical chopper part 213 and directed to the emission end 201 for the laser light. The laser light 218 for collimation is emitted from the laser emission end 201 and caused to intermittently irradiate the object 200 to be surgically operated. The light reflected from the object 200 to be surgically operated by said intermittent irradiation and the external light (the reflect light comprising only that of the external light while the intermittent collimation laser light 218 is not emitted to the object 200 to be surgically operated) are provided to the inner layer optical fibers 215 and the outer layer optical fibers 217 depending on the position of the object 200 to be surgically operated. The reflect light conducted and provided respectively by said inner layer optical fibers 215 and the outer layer optical fibers 217 are respectively received by the light detectors 202 and 203. The output signals of which magnitude depends on the light value provided by the light detectors 202 and 203 are amplified respectively by the preamplifiers 204 and 205 so that the differential output of said output signals is picked up by the differential amplifier 206. The lock-in amplifier 207 is adapted to receive said AC differential output and provides the approximated DC output by excluding the differential component of the noise signal affected by the external light in accordance with the phase of the modulated signal received from the optical chopper part 213. The output of the lock-in amplifier 207 is converted to the positive signal when the irradiated position on the object 200 to be surgically operated is closer to the side of the orientation cylinder 216 than the position of the indefinite distance range (cf. $\Delta l_1$ in FIG. 4) to be determined by the orientation cylinder 216 and described later in connection with FIG. 4 while it becomes a negative signal when said irradiated position is farther from the orientation cylinder 216 than position within said indefinite distance range. When said irradiated position is within said indefinite distance range, the output of the lock-in amplifier 207 becomes an indefinite signal either O, positive or negative depending on the reflective condition of the object 200 to be surgically operated as it will be explained later. The comparator 208 provides the output as the result of comparison between the output of the lock-in amplifier 207 and the reference value, for example OV. Depending on the result of said comparison, a signal of lower level is provided if the output of the lock-in amplifier 207 is a positive signal and a signal of higher level is provided if said output is a signal of less than OV. The laser control part 209 is adapted to control the laser power supply source 210 in such a manner that the oscillation tube part 211 for providing the laser for surgical operation may be caused to oscillate only when the signal of lower level is provided by the comparator 208. Thus, when the output of the comparator 208 is at a lower level, the oscillation tube part 211 for supplying the laser for surgical operation is caused to oscillate so as to supply the laser for surgical operation. The laser for surgical operation is conducted by the multi-articulation mirror and emitted out of the laser emission end 201 in combination with the laser light 218 for collimation whereby the former laser will irradiate the portion of the object 200 to be surgically operated where the laser 218 for collimation irradiates. Because of this irradiation, the object 200 to be surgically operated may be removed by burning it with the laser light for surgical operation.

Fig. 4 shows said indefinite distance range to be determined by said orientation cylinder 216. In Fig. 4, numeral 215 designates the inner layer optical fibers; numeral 215A the inner-most-edge of the input end of said inner layer optical fibers 215; numeral 216 the orientation cylinder; numeral 216A the outer-most-edge of the opening of said orientation cylinder 216; numeral 216B the inner-most-edge of the opening of the orientation cylinder 216; numeral 217 the outer layer optical fiber; numeral 217A the outer-most-edge of the input end of the outer layer optical fiber 217; and numeral 218 the laser light for collimation. The boundary line at which the inner layer optical fibers 215 may receive the reflected light of the laser light 218 for collimation is limited by the line $L_1$ which is defined by connecting the extension of the edge 215A and the edge 216B. In other words, the reflected light derived from the position at upper side from said line $L_1$, that is the position closer to the opening of the orientation cylinder 216 than the boundary line formed by the line $L_1$, may be received by the inner layer optical fibers 215, while the reflected light derived from the position at lower side from said line $L_1$ will be interrupted by the orientation cylinder 216, so that it will not be received by the inner layer optical fibers 215. Similarly, the boundary line at which the outer layer optical fibers 217 may receive the reflected light of the laser light 218 for collimation is limited by the line $L_2$ which is defined by connecting the edge 217A and the edge 216A. The reflected light which comes from the upper side than said line $L_2$ will be interrupted by the orientation cylinder 216 and not received by the outer layer optical fibers 217 while the reflected light coming from the position at lower side than said line $L_2$ or farther from the opening of the orientation cylinder 216 with the line $L_2$ as the boundary line may be received by the outer layer optical fibers 217. Accordingly, the reflected light derived from the region A indicated by hatching which is defined by the lines $L_1$ and $L_2$ may be received by both the inner layer optical fibers 215 and the outer layer optical fibers 217. Numerals 219 and 220 respectively represent the point where the laser light for collimation 218 crosses with the line $L_2$ and the line $L_1$. The distance range $\Delta l_1$ defined by said crossing points 219 and 220 represents the indefinite distance range defined by the abovementioned orientation cylinder 216. As long as the object 200 to be surgically operated is located within said indefinite distance range $\Delta l_1$, both the inner layer optical fibers 215 and the outer layer optical fibers 217 may receive the reflected light of the laser light 218 from the object 200 to be surgically operated. However, the light values received by said optical fibers are not necessarily the same depending on the surface condition of the object to be surgically operated. Especially when the surface of the object 200 to be surgically operated contain certain glitterness and the reflected light involves much of the light component reflected by the mirror, the nature of the output signal provided by the lock-in amplifier 207 as shown in FIG. 2 or the position determined by the comparator 208 may be subject to variation depending on which optical fibers, the inner layer optical fibers 215 or the outer layer optical fibers 217 will receive said reflected light. In other words, the indefinite distance range $\Delta l_1$ serves as the erroneous range for the position determination. If the irradiated position of the object 200 to be surgically operated is located closer to the side of the opening of the orientation cylinder 216 than the crossing point 219, the reflected light of the laser light 218 for collimation is received only by the inner layer optical fibers 215 and the lase light for surgical operation is provided as earlier explained. On the contrary, if the irradiated position of the object 200 to be surgically operated is located at a position farther from the opening of the orientation cylinder 216 than the crossing point 220, the reflected light of the laser light 218 for collimation is received only by the outer layer optical fibers 217, the laser light for surgical operation will not be provided as earlier mentioned.

Now coming back to FIG. 1, it is assumed that the configuration of the tip end of the outer cylinder 109 is made the same as that of the tip end of the hollow cylindrical body 214 and the inner layer optical fibers 215, the orientation cylinder 216 and the outer layer optical fibers 217 are attached at the outer periphery of said tip end portion as shown in FIG. 3.

FIG. 5 shows the indefinite distance range when the orientation cylinder 216 and so forth are applied to be emission end for laser light of the laser scalpel shown in FIG. 1. Since numerals 215, 215A, 216, 216A, 216B, 217, 217A, 110 and 111, and the symbols $L_1$, $L_2$, A and $\Delta l_1$ have been explained, the explanation thereof will not be repeated here. The laser light 110 or 111 for collimation is inclined similarly to the inclination of the orientation cylinder 216 and to the inclination of the boundary lines $L_1$ and $L_2$. Accordingly, the crossing points defined by the laser light 110 for collimation or the laser light 111 and the boundary lines $L_1$ and $L_2$ are respectively represented by 114 and 113. The indefinite distance range $\Delta l_2$ defined between the crossing point 113 and the crossing point 114 becomes naturally larger than the range $\Delta l_1$ and this means that the distance in which the indefinite position determination has to be done will be correspondingly much larger, causing the apparatus in question to be less practical. In other words, if an apparatus for preventing erroneous emission for the laser scalpel of a multi-articulation mirror manipulator type is applied directly to the apparatus for preventing erroneous emission for the laser scalpel of an optical fiber type, there has been such a problem wherein the indefinite distance range in which the position determination which justifies the emission of the laser light for surgical operation has to be indefinite will be wider thus making it impossible for the apparatus to be put into practical use.

SUMMARY OF THE INVENTION

Accordingly, the primary object of the present invention is to provide an emission end of an infrared fiber cable which does not deteriorate the photosensitive infrared fiber and is excellent in maneuvability.

Further object of the present invention is to provide an apparatus for preventing erroneous emission for a laser scalpel of an optical fiber type attachable to a laser scalpel of an infrared fiber type by providing the light emission part for the collimation light around the emission end of the laser and by controlling the emission of the laser light for collimation and the detection of the reflected light thereof in accordance with the direction of laser light emission and the orientation of the detection part.

Still another object of the present invention is to provide an apparatus for preventing erroneous emission for a laser scalpel of an optical fiber type which is applicable also to a laser scalpel of an optical fiber type by appropriating the indefinite distance range of the emission end for the laser light in which the position determination justifying the emission of the laser light for surgical operation has to be indefinite.

The infrared fiber cable according to the present invention comprises means for emitting a light for collimation which is a visible light, an infrared fiber accommodated in a protective tube adapted to interrupt said light for collimation and a member adapted to allow the infrared light beam emitted from said infrared fiber to pass therethrough but to reflect the light for collimation, said infrared light beam being transmitted from one surface of said member and said light for collimation being emitted against the opposite surface of said member and reflected therefrom.

According to the present invention, since the infrared fiber is separated from the light for collimation by means of said protective tube and said member, the infrared fiber will not be affected by the light for collimation, and further the infrared light beam is allowed to pass through said member while the light for collimation is reflected, both of said lights may be emitted in the same direction.

In the apparatus for preventing erroneous emission of a laser light according to the present invention, the light for collimation is emitted to the object to be irradiated from the circumference of the emission end for the laser light, plural pairs of light detectors for receiving the reflected light of said light for collimation are disposed around the circumference of said emission end for laser light, the difference of the output signals provided by said light detectors is picked up by a differential amplifier so that the distance between the emission end for laser light and the object to be irradiated may be detected by the distance detecting part, and emission by a laser scalpel against the object to be irradiated is controlled by feed-back control means in accordance with the output signal as the result of said detection.

Accordingly, since the light for collimation is emitted from the emission end for laser light, emission of the light for collimation and detection of the reflected light thereof are controlled in accordance with the direction of light emission and the orientation of the light detectors and a light emitting part and plural pairs of light detectors are provided around the circumference of the emission end for laser light so that the output of said light detectors may be picked up in the form of an output signal by way of an adder adapted to approximate the outputs of said light detectors, said distance between the emission end and the object to be irradiated may be accurately detected even if the reflected light from the object may be diversified.

The apparatus for preventing erroneous emission for the laser scalpel of an optical fiber type according to the present invention, when used for a laser scalpel in which the invisible laser light for surgical operation is conducted by an optical fiber so as to irradiate the object to be surgically operated thereby removing said object by burning it, is adapted to provide a visible light for collimation by means for supplying a visible light in the form of a light beam, and is of such a construction that a special mirror is disposed in front of the emission end of an optical fiber so inclined that the laser light for surgical operation is transmitted therethrough and the visible light for collimation provided in a condensed condition by said means for providing the visible light is reflected so as to conduct said reflected visible light substantially onto the optical axis of the laser light for surgical operation, a light receiving part provided with two kinds of openings is arranged at the means for receiving the light, said light receiving part being adapted to receive the visible light reflected from the object to be surgically operated, said light receiving part is adapted to receive the reflected visible light according to the position of said object to be surgically operated and provide electrical signals corresponding to the respective light value of the received lights, the difference of two outputs provided by said light receiving means is picked up by means for determining the position of the object to be surgically operated so as to determine the position of said object in accordance with said difference signals, and the output of the laser light for surgical operation is controlled by feed-back control means in accordance with the position determining output derived from said means for determining the position of the object.

The special mirror according to the present invention allows the laser light for surgical operation conducted by and emitted out of the optical fiber to pass therethrough but reflects the visible light for collimation emitted by the means for providing the visible light, and directs the reflected visible light substantially onto the optical axis of the transmitted laser light for surgical operation whereby the visible light directed substantially onto the optical axis of the laser light for surgical operation may provide the same effect as emission of the laser for collimation provided by a conventional laser scalpel, for example a laser scalpel of a multi-articulation mirror manipulator type. Thus even if the conventional apparatus for preventing erroneous emission for a laser scalpel in which the output of the laser for surgical operation is controlled in accordance with detection of the position for the object based on the light value of the received visible light reflected by the object to be surgically operated is applied to an apparatus for preventing erroneous emission for the laser scalpel of an optical fiber type, the indefinite distance range which causes the detection of the position of the object to be indefinite may be equivalent to that of the conventional laser scalpel.

The infrared fiber cable according to the present invention includes means for emitting the light for collimation and a protection tube to accommodate the infrared fiber, and is so adapted as to emit the infrared light beam and the light for collimation in the same direction without causing the laser for collimation to collide with the infrared fiber by means of a member which allows the infrared light beam emitted from the infrared fiber to be transmitted therethrough and reflects the light for collimation whereby such an effect may be obtained that the infrared fiber being photosensitive may not be deteriorated if used. Further since means for emitting the light for collimation is incorporated, both the light for collimation and the infrared beam may be emitted from one emission end, thereby providing such an effect as to improve maneuvability of the apparatus.

According to the present invention, since the light for collimation is irradiated around the circumference of the laser emission end and the light receiving part is so arranged that emission of the light for collimation and detection of the reflected light are controlled in accordance with the direction of light emission and the orientation of the light detectors, such an effect may be obtained that the apparatus for preventing erroneous emission for a laser scalpel of an optical fiber type may be provided which can be mounted to a laser scalpel of an infrared fiber type.

Further according to the present invention, a special mirror adapted to allow the laser for surgical operation to be transmitted therethrough but reflect the light for collimation is used and so constructed as to direct the light for collimation substantially onto the optical axis of the laser for surgical operation whereby an apparatus for preventing erroneous emission may be provided which can be attached to a laser scalpel of an infrared fiber type and the indefinite distance range may be equivalent to that of a laser scalpel of a multi-articulation mirror manipulator type, the laser for surgical operation may be emitted in a stable condition and as the result an apparatus safe in operation may be obtained.

These and other objects and the advantages of the present invention will appear more clearly from the following detailed disclosure read in conjunction with the accompanying drawings.

BRIEF EXPLANATION OF THE DRAWINGS

FIG. 3 is the vertical sectional view showing the emission end for a laser light for a conventional laser scalpel;

FIG. 4 is an explanatory illustration showing the manner of incidence of a light by an optical fiber in accordance with the positional relationship between the light beam for collimation and the object to be surgically operated;

FIG. 6 is the vertical sectional view showing the first embodiment of the infrared fiber cable according to the present invention;

FIG. 7 is the vertical sectional view showing the second embodiment of the infrared fiber cable according to the present invention;

FIG. 17 is the vertical sectional view showing the emission end for a laser light according to the second embodiment of the present invention as shown in FIG. 16;

FIG. 19 is the vertical sectional view showing the emission end for a laser light according to the third embodiment of the present invention as shown in FIG. 18.

DESCRIPTION OF THE PREFERRED EMBODIMENTS

Figure 1:
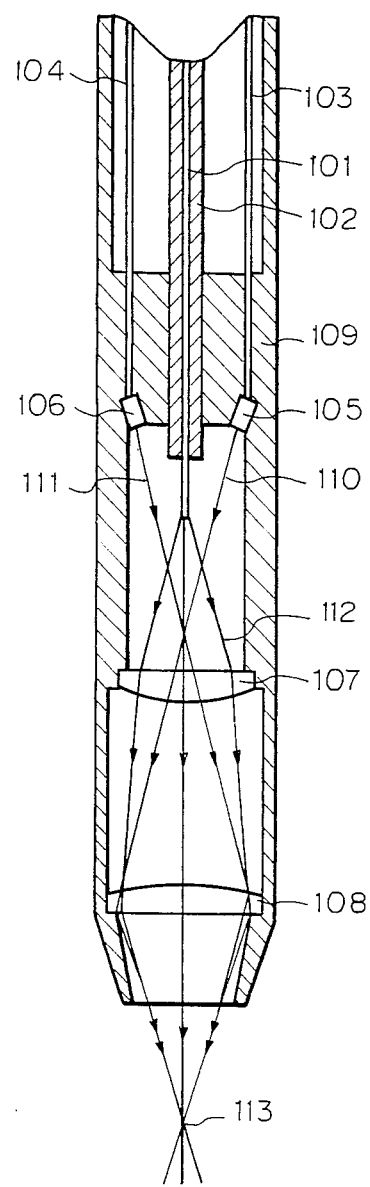
FIG. 1 is the vertical sectional view of the emission end for a laser light showing the conventional manner in which the light for collimation is directed to a laser scalpel of an optical fiber type.
Figure 5:
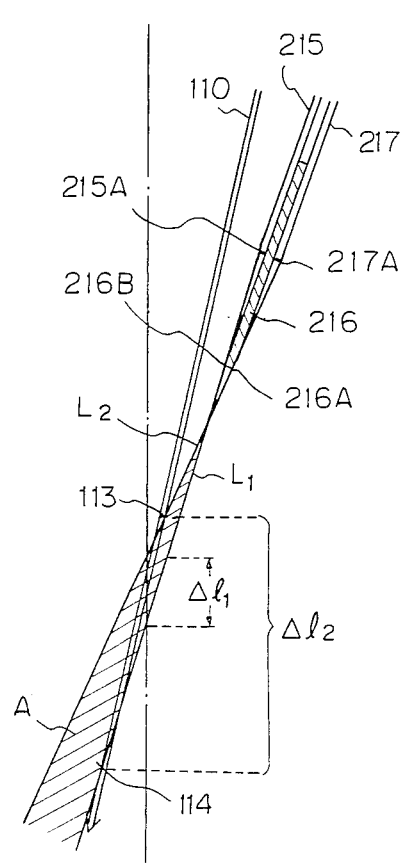
FIG. 5 is an explanatory illustration of the indefinite distance range caused by the apparatus in FIG. 1.

Firstly, the infrared fiber cable according to the present invention will be explained. FIG. 6 is the vertical sectional view showing the first embodiment of the present invention. In FIG. 6, numerals 101, 103, 104, 112, 110 and 111 designate the same elements as those of the infrared fiber cable according to the prior art. Numeral 1 designates the casing for the emission end; numerals 2 and 2a micro lenses provided at the inside of said casing 1 for the emission end; and numerals 3 and 3a mirrors for the light for collimation which are located along the optical axis of the light beams 110 and 111 passing through said micro lenses 2, 2a and provided at the end portion of said casing 1 for the emission end in the opposite to said micro lenses 2, 2a and inclined downwardly. Numeral 4 designates the protective tube adapted to isolate the infrared fiber 101 from the light beam 110 for collimation; numeral 5 fixture member adapted to fix the end of the infrared fiber 101 provided within said protective tube 4; and numeral 6 a window member fixed so as to close the end portion of the protective tube 4 and adapted to allow the infrared light beam 112 to be transmitted therethrough but to reflect the light beam 110 for collimation which is a visible light.

According to the infrared fiber cable constructed as above explained, when the lights for collimation are transmitted respectively to the fibers 103, 104 for the light for collimation and emitted in parallel to each other through the micro lenses 2, 2a in the form of the light beams 110, 111 for collimation, said light beams 110, 111 for collimation will proceed straightforwardly until they are reflected by the mirrors 3, 3a disposed obliquely downwardly and then collide against the window member 6 to be reflected again obliquely downwardly. Thus, the light beams 110, 111 for collimation emitted outwardly by the window member 6 out of the emission end of the infrared fiber in the same direction as the infrared light beam 112 are caused to cross each other outwardly of the emission end so as to form the focal point.

According to this embodiment, the infrared fiber 101 is accommodated in the protective tube 4 and the end portion of said infrared fiber 101 is disposed inside of said window member 6, and further the light beams 110, 111 are reflected by the window member 6 so that the infrared fiber 101 may not be deteriorated by the light beams 110, 111 for collimation.

Further, the direction of the light beams 110, 111 for collimation may be adjustable by changing the positions of the mirrors 3, 3a and the window member 6 and/or the angles of installation of these members.

FIG. 7 shows the second embodiment of the present invention wherein in addition to the casing 1 for the emission end, a condensing lens 7 is so provided and adjusted that any of the infrared light beam 112 and the light beams 110, 111 for collimation may be condensed at the identical condensing point 8. It is to be noted that the reason why the condensing point 8 may be identical by means of one condensing lens 7 is to have utilized difference of the wave lengths between the infrared light beam 112 and the light beams 110, 111 which makes the focal distance of the condensing lens 7 to be different.

Figure 8:
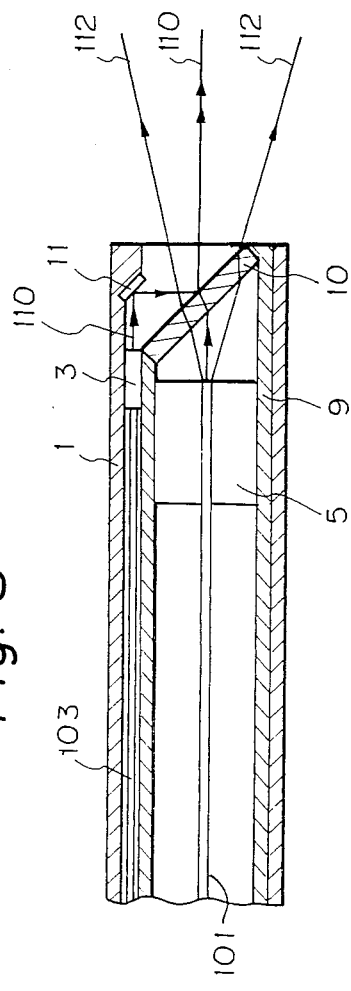
FIG. 8 is the vertical sectional view showing the third embodiment of the infrared fiber cable according to the present invention.
Figure 9:
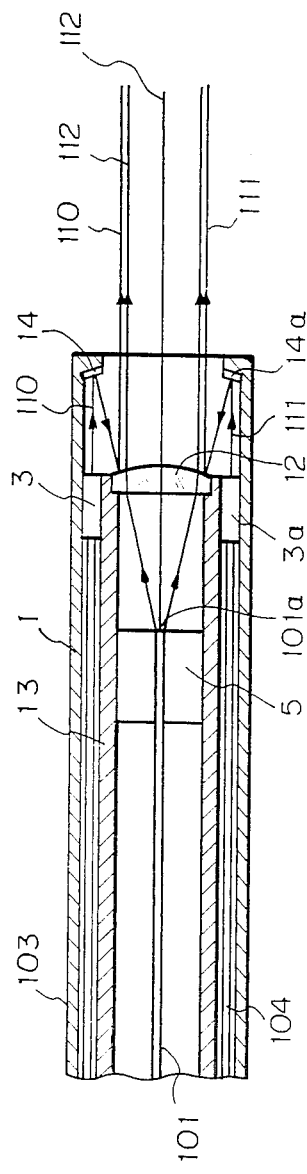
FIG. 9 is the vertical sectional view showing the fourth embodiment of the infrared fiber cable according to the present invention.

FIG. 8 shows the third embodiment of the present invention wherein the window member 10 is provided at the end portion of the protective tube 9 at the angle of 45 degrees and the mirror 11 is also disposed at the angle of 45 degrees relative to said end portion. Because of this arrangement, the light beam 110 for collimation emitted in the horizontal direction is reflected by the mirror 11 in the vertical direction and then collides against the window member 10 to be reflected in the horizontal direction. On the other hand, the infrared light beam 112 is expanded after having passed through the window member 10 due to inclined installation of the window member 10 at the angle of 45 degrees. In this manner, if the light beam 110 for collimation is so adjusted as to be directed centrally of the infrared light beam 112, the light beam 110 which proceeds straightforwardly may be utilized for various purposes. It is further to be noted that the relationship between said light beam 110 for collimation and the infrared light beam 112 is substantially the same as the introduction of the collimation light at the optical path in the multi-articulation mirror manipulator. The fourth embodiment shown in FIG. 9 is different from any one of the above-mentioned embodiments and utilizes a lens in place of the window members 6, 10. In this embodiment, numeral 12 designates a convex lens provided at the end portion of the protective tube 13. When said convex lens 12 is so positioned that the convex surface thereof is faced to the side of the mirrors 14, 14a and the emission end 101a for the infrared fiber 101 is disposed at the foscal point of said convex lens 12, the infrared light beam 112 emitted will become a substantially parallel light after having passed through the convex lens 12. On the other hand, the light beams 110, 111 are reflected by the mirrors 14, 14a to be incident upon the convex surface. By appropriately selecting the inclination angle of the mirrors 14, 14a, the light beams 110, 111 reflected by said convex surface may be directed in parallel with the optical axis of the infrared beam 112 and the diameter thereof may be substantially the same as that of the infrared beam 112. Although a convex lens 12 is utilized in FIG. 9, a lens having a concave or a plain surface at the side of the mirrors 14, 14a may be used as the reflection surface for the visible light beams 110, 111 for collimation.

In the respective embodiments as above mentioned, the light for collimation is transmitted by the fibers 103, 104 for collimation light and the light beams 110, 111 are thereby emitted. Similar effects to those of the respective embodiments as above mentioned may be obtained if such light emitting elements as a light emitting diode, a laser diode or the like are disposed at the positions of the fibers 103, 104 for collimation and the light provided by such light emitting elements in utilized.

Figure 2:
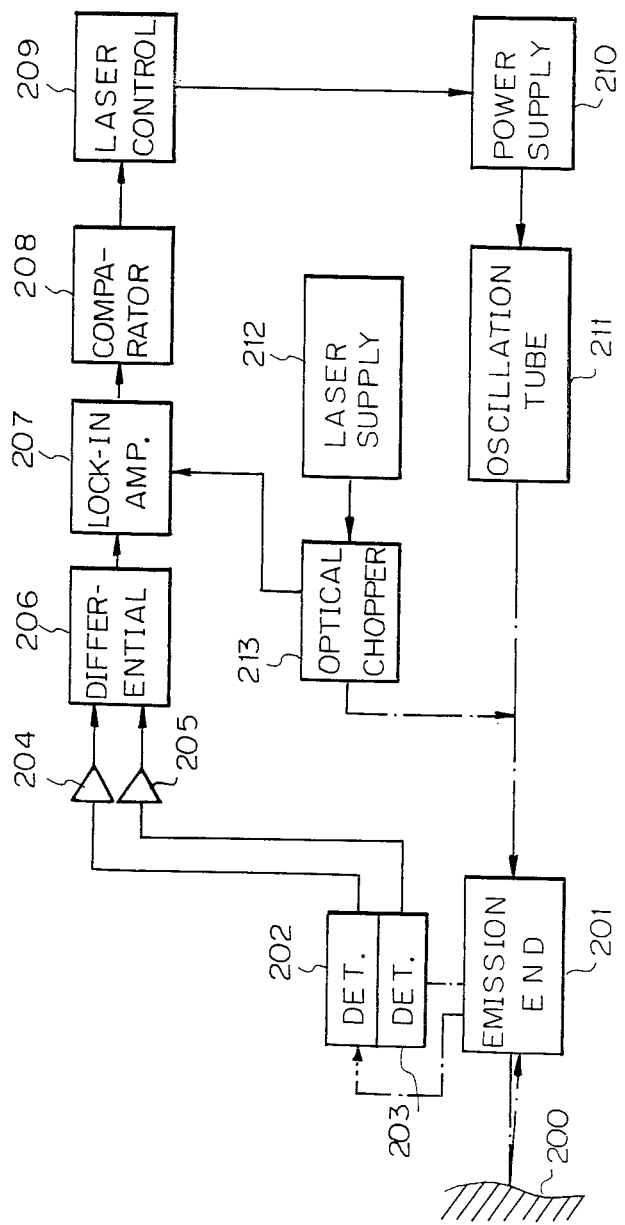
FIG. 2 is a block diagram showing an apparatus for preventing erroneous emission for a conventional laser scalpel.
Figure 10:
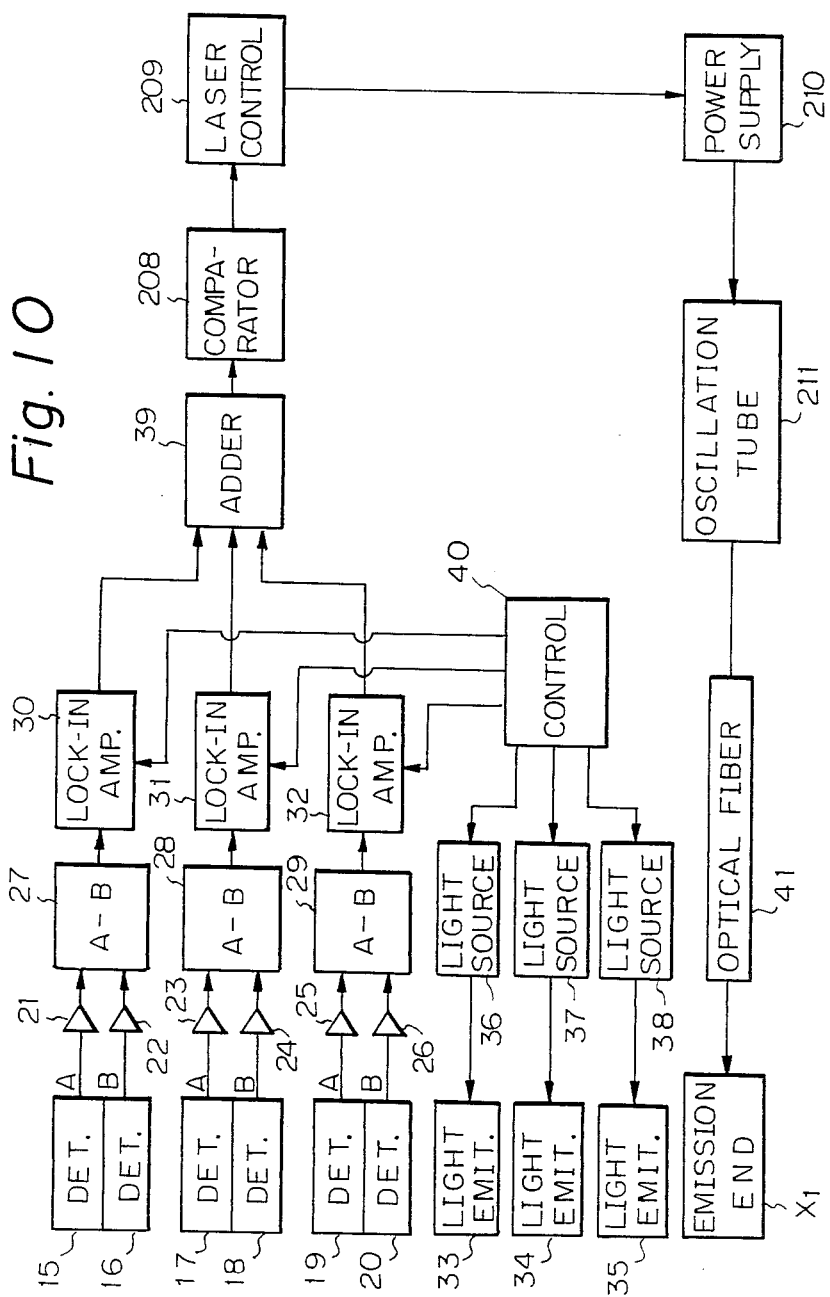
FIG. 10 is the block diagram showing the first embodiment of the apparatus for preventing erroneous emission for a laser scalpel of an optical fiber type according to the present invention.
Figure 11:
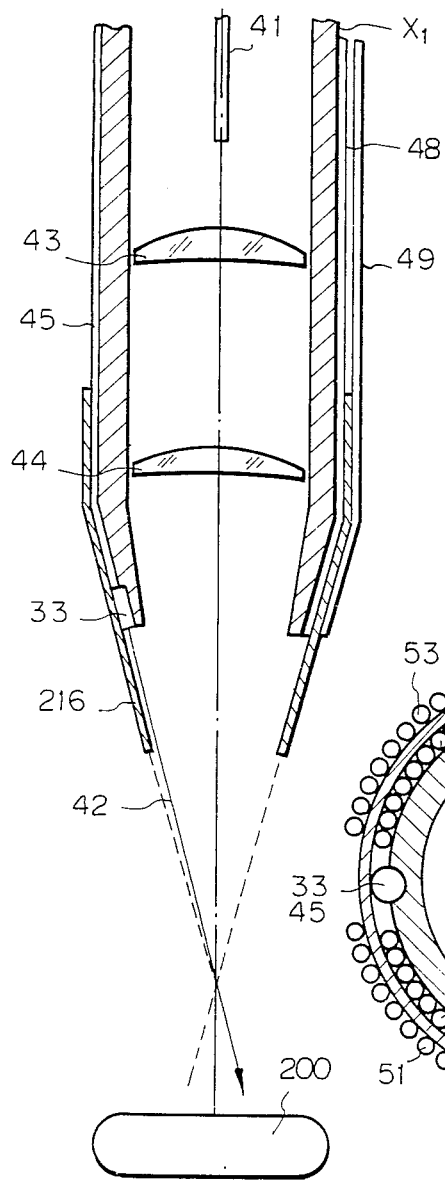
FIG. 11 is the vertical sectional view showing the emission end for a laser according to the first embodiment of the present invention as shown in FIG. 10.
Figure 12:
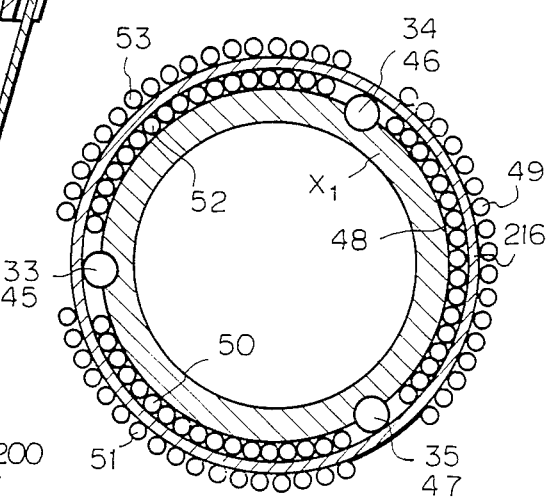
FIG. 12 is the horizontal sectional view showing the arrangement of the light emitting part and the light receiving part in connection with the emission end for a laser light as shown in FIG. 11.

The first embodiment of an apparatus for preventing erroneous emission according to the present invention will next be explained. In the relative drawings, identical members to those shown in FIGS. 2 and 3 are to be designated by the same reference numbers. In FIG. 10, numerals 15, 16, 17, 18, 19, 20 designate three paris of light detectors; numerals 21, 22, 23, 24, 25, 26 preamplifiers; numerals 27, 28, 29 differential amplifiers; numerals 30, 31, 32 lock-in amplifiers; numerals 33, 34, 35 light emitting part comprising micro lenses and the like; numerals 36, 37, 38 light sources for providing lights for collimation; numeral 39 an adder to add the outputs of three lock-in amplifiers; numeral 40 a control part adapted to control the light source for the light for collimation such as a light emitting diode and simultaneously feed the signals thereof to the lock-in amplifiers; and numeral 41 an optical fiber to direct the laser light for surgical operation to the laser emission end $X_1$. It is to be noted that the light emission part for the light for collimation and the light detecting part may be constructed for example as shown in FIG. 11 and FIG. 12. In these figures, numeral 42 designates the light for collimation; numerals 43, 44 condensing lenses adapted to condense the laser light for surgical operation which is emitted from the optical fiber 41; numerals 45, 46, 47 optical fibers for the light for collimation adapted to conduct the light from the light source 36 for the light for collimation to the light emitting part 33; and numerals 48, 49, 50, 51, 52, 53 a group of optical fibers for receiving the lights which are grouped and connected to the light detectors 15, 16, 17, 18, 19, 20.

Figure 13:
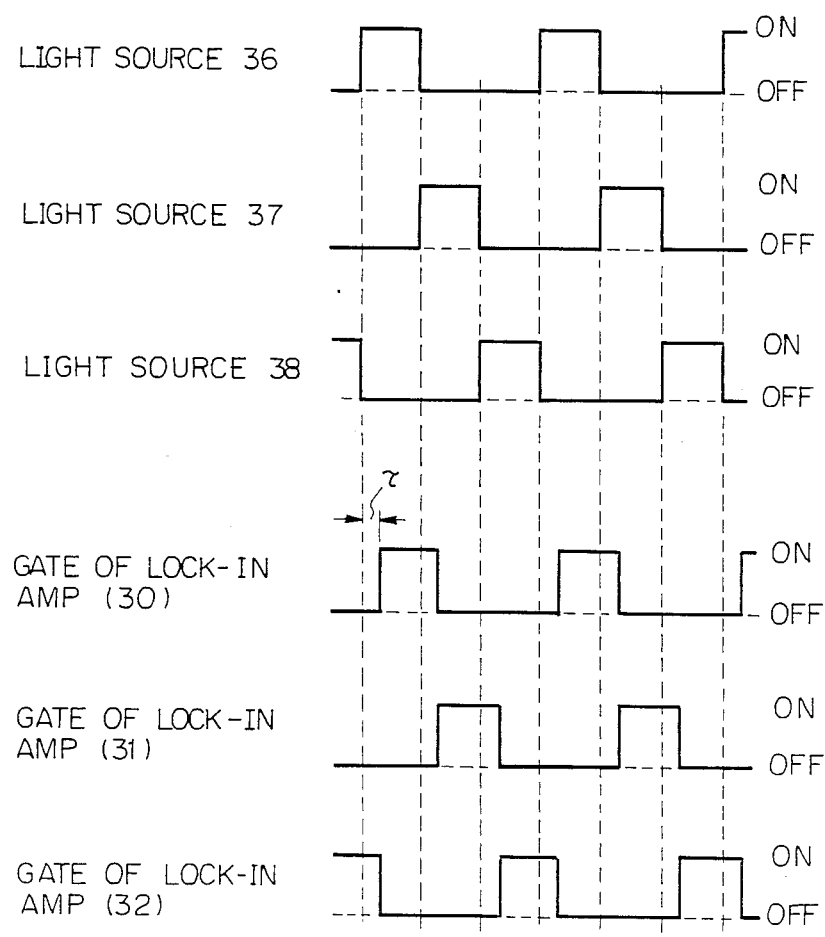
FIG. 13 is the timing chart at the gate of the lock-in amplifier for the apparatus for preventing erroneous emission as shown in FIG. 10.
Figure 14:
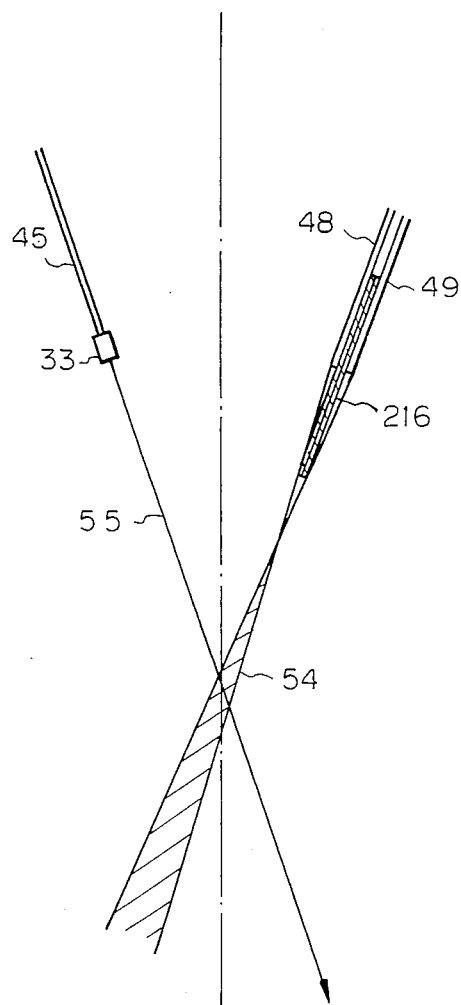
FIG. 14 and FIG. 15 are explanatory illustration showing how the errors of the distance setting will be varied depending on the positional relationship between the light emitting part and the light receiving part.
Figure 15:
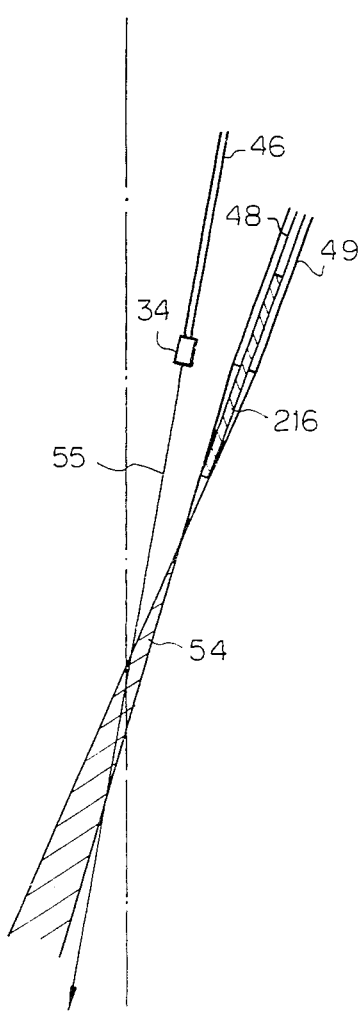

Operation of the apparatus according to this embodiment will now be explained. The light sources 36, 37, 38 for the light for collimation are turned ON and OFF by the control part 40 for the light for collimation in the sequence as shown in FIG. 13. Thus the lights to be emitted for collimation are conducted by the optical fibers 45, 46, 47 to the light emitting parts 33, 34, 35 and emitted against the object 200. The lights reflected by said object 200 are received respectively by a group of optical fibers 48, 49, 50, 51, 52, 53 to receive such lights and are converted into the electrical signals at the light detectors 15, 16, 17, 18, 19, 20 and fed into the differential amplifiers 27, 28 29 by way of the preamplifiers 21, 22, 23, 24, 25, 26. At the differential amplifiers 27, 28, 29, respective differential output for the respective pairs of the preamplifiers are provided and then supplied to the lock-in amplifiers 30, 31, 32 (the parts for determining the distances). The gates of said lock-in amplifiers are set so as to operate after the time delay $\tau$ which is provided of the relative circuits and so forth from the ON-OFF timing of the corresponding light sources. As the result, among the lights received by the group of fibers 48, 49 for receiving the light, only the component of the reflected light provided by the light source 36 for the light for collimation may be obtained as the output of the lock-in amplifier 30. Similarly, only the component of the reflected lights emitted by the light sources 37 and 38 may be obtained as the output of the lock-in amplifiers 31 and 32. In this manner, the positional relationship shown in FIG. 14 may be substantially maintained between the light emitting part and the light receiving part. Namely, the distance of the light 55 for collimation crossing the area 54 for the reflected light to be received by both of the inner layer fibers and the outer layer fibers corresponds to the error in setting the distance of the present apparatus. In this case, such a distance may be kept small as shown in FIG. 14. If the gates for the lock-in amplifiers 30, 31, 32 do not operate as shown in FIG. 13, such a positional relationship as shown in FIG. 15 will be caused between the light emitting part 33 for the light for collimation and be light receiving part which results in much larger error in setting the distance.

Thus, the outputs of the lock-in amplifiers serving as the distance determining part will become positive when the object 200 to be irradiated is located at a position near to the crossing point between the extension of the orientation cylinder 216 and the light 42 for collimation while it will become negative when the object is located at a position farther from said crossing point. If the front surface of the object 200 is uneven, nature of said outputs, i.e., positive or negative may be reversed depending on the direction of the received light. However, by adding the outputs of the lock-in amplifiers 30, 31, 32 with the adder 39, the variation of the lights received from three different direction may be approximated. Then, by determining the output of said adder 39 to be positive or negative with the comparator 208, the emission signal will be fed to the power supply source 210 for the laser if the comparator 208 indicates it to be positive while the stop signal will be transmitted to the power supply source 210 for the laser if the negative nature is detected.

By this sort of operation, only when the object to be irradiated is located nearer than the distance determined by the light emitting part and the orientation cylinder, it will become possible for the laser to be emitted.

It is to be noted that an example of using three sets of the light emitting parts and the light receiving parts has been explained in the above-explained embodiment, but any number of sets of these parts may be applicable if more than two sets.

It is also to be noted that in the above-mentioned embodiment, although the light for collimation has been conducted from the light sources to the light emitting parts by means of optical fibers, the light sources may be directly disposed at the position of the light emitting parts.

It is further to be noted that although the optical fibers have been used at the light receiving parts in the above-mentioned embodiment the light detectors may be disposed directly at the position of the light receiving parts.

Figure 16:
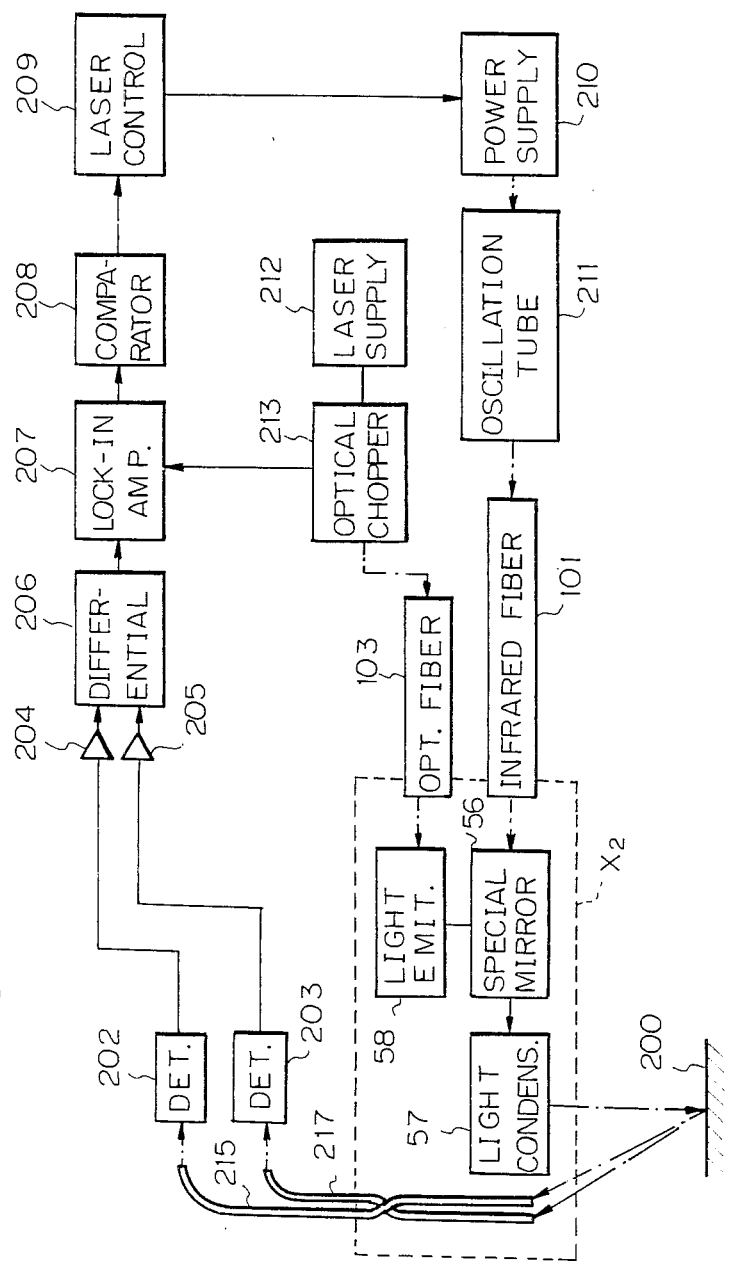
FIG. 16 is the block diagram showing the second embodiment of the apparatus for preventing erroneous emission for a laser scalpel of an optical fiber type according to the present invention.

Other embodiments of an apparatus for preventing erroneous emission will next be explained with reference to the accompanying drawings. FIG. 16 illustrates the entire construction of the apparatus in a block diagram. In FIG. 16, numerals 200, 202–213, 215 and 217 designate the corresponding members to those shown in FIG. 2 having the same functions and the construction of these members are the same as those of the prior art as explained earlier. In FIG. 16, numeral 200 designates the object to be surgically operated; numerals 202, 203 light detectors; numerals 204, 205 preamplifiers; numeral 206 a differential amplifier; numeral 207 a lock-in amplifier; numeral 208 a comparator; numeral 209 a laser control part; numeral 210 a power supply source for the laser; numeral 211 an oscillation tube part for providing a laser for surgical operation; numeral 212 the laser supply source for collimation; numeral 213 the optical chopper part; numeral 215 inner layer optical fibers; and numeral 217 outer layer optical fibers. For convenience of illustration, the inner layer optical fibers 215 and the outer layer optical fibers 217 are represented respectively as a single fiber. Numeral 101 is the infrared fiber which allows the infrared light such as a $CO_2$ laser light as the laser light for surgical operation to pass through, but is unable to transmit the visible light. The input end of the infrared fiber 101 is optically connected to the output part of the oscillation tube part 211 for providing the laser for surgical operation by way of an optical system comprising a condensing lens (not shown) and so forth. Numeral 103 designates a optical fiber for the light for collimation adapted to conduct the visible light as the laser light for collimation such as a He-Ne laser light. The input end of said optical fiber is optically connected to the optical output part of the optical chopper part 213 by way of an optical system comprising a condensing lens (not shown) and so forth. An example of such an infrared fiber 101 is a Tl Br-Tl I fiber having a diameter of 0.5 mm$\phi$. Numeral $X_2$ designates the light emission end for the laser light which serves to conduct the laser light for surgical operation from the infrared fiber 101 and the laser light for collimation from the optical fiber 103 for the collimation light and emit these laser lights to the object 200 to be surgically operated and direct the reflected light of said light for collimation to the inner layer optical fibers 215 and the outer layer optical fibers 217. The construction of said laser light emission end is as shown in FIG. 17. Numeral 56 designates a special mirror made of Ge material for example; numeral 57 an optical system for condensing the light; and numeral 58 an optical syste for emitting the light. The detailed explanation about these elements will be made in conjunction with FIG. 17. The laser emission end $X_2$ is consisted of the elements as above mentioned, the inner layer optical fibers 215, the outer layer optical fibers 217, the infrared fiber 101 and the tip end portion of the optical fiber 103 for the light for collimation.

FIG. 17 shows in the vertical section the construction of the emission end $X_2$ for the laser light shown in FIG. 16. In FIG. 17, numeral 59 designates the outer cylinder of which outer configuration is the same as the configuration of the outer wall of the hollow cylindrical body 214 shown in FIG. 3. Along the outer wall of said outer cylinder 59 are arranged in a similar manner to the prior art shown in FIG. 3, a multiplicity of the inner layer optical fibers 215, the orientation cylinder 216 around the outer periphery of the tip end portion of said inner layer optical fibers 215 and a multiplicity of the outer layer optical fibers 217 around the outer periphery of said orientation cylinder 216. Numeral 60 designates an inner cylindrical body of which outer diameter is smaller than the inner diameter of said outer cylinder 59 and is secured to the outer cylinder 59 with the outer wall being in contact with the inner wall of the outer cylinder 59. Numeral 61 designates a fixture member secured to the interior of the inner cylinder 60 at a position adjacent to the end portion of the inner cylinder 60 and fixing the infrared fiber 101 substantially at the output end thereof. Numeral 56 designates a special mirror which allows the laser light for surgical operation emitted out of the infrared fiber 101 to be transmitted therethrough but reflects the laser light for collimation emitted out of the optical fiber 103 for the collimation light. Said special mirror is provided at the position to receive the output light from the infrared fiber 101, and supported at the end of the inner cylinder 60 in an inclined position. It is to be noted that said special mirror 56 has parallel surfaces and is so arranged that the indication angle is determined so as to form about 45 degrees inclination between said parallel surfaces and the optical axis of the infrared fiber 101. The optical fiber 103 for the light for collimation is disposed in the clearance define by the outside of the inner cylinder 60 and the inside of the outer cylinder 59. Numeral 62A designates the micro lens disposed at the position to receive the output light from the output end of the optical fiber 103 for the light for collimation. Numeral 62B designates a mirror which is disposed at the position to receive the output light from the micro lens 62A and secure to the inclined inner wall of the outer cylinder 59. The reflection surface of said mirror 62A is disposed in parallel to the reflection surface of said special mirror 56. It is to be understood that the position where the laser light for surgical operation at the optical axis of the output end of the infrared fiber 101 is refracted, transmitted and then emitted by the special mirror 56 corresponds to the position where the laser light 218 for collimation emitted from the micro lens 62A is reflected by the mirror 62B and then reflected again by the special mirror 56. Accordingly the laser light 218 for collimation after reflected by the special mirror 56 is found substantially along the optical axis 63 of the laser light for surgical operation which has been transmitted through the special mirror 56. Numerals 107, 108 designate the condensing lenses such as Zn-Se lenses which are disposed in front of the position to receive the laser light for surgical operation and the laser light for collimation from the special mirror 56 and carried by the outer cylinder 59. Said condensing lenses, having the optical axis coinciding with the optical axis 63, serve to condense the light for surgical operation in front of the laser light emission end $X_2$. It is to be noted that the optical axis of the inner layer optical fibers 215, the optical axis of the outer layer optical fibers 217 and the extension of the inclined surface of the orientation cylinder 216 are respectively converged substantially into the optical axis 63. It is also to be noted that said light condensing optical system 57 comprises two condensing lenses 107, 108 and the light emitting optical system 58 comprises the micro lens 62A and the mirror 62B. The intermediate infrared fibers 101 and the optical fibers 103 for the light for collimation except those provided in the outer cylinder 59 at the laser light emission end $X_2$ are covered with the outer cover and formed into a flexible cable. It is to be understood that the positional relationship for laser emission among the inner layer optical fibers 215, the orientation cylinder 216, the outer layer optical fibers 217 and the laser light 218 for collimation are similar to those of the prior art as shown in FIG. 4 and that the indefinite distance range $\Delta l_1$ described in connection with FIG. 4 may be also applicable to the case in FIG. 17.

The operation of the present invention will next be explained. The laser light 218 provided by the optical chopper part 213 is directed to the laser light emission end $X_2$ by means of the optical fiber 103 for the light for collimation. On the other hand, the laser light 218 for collimation emitted by the optical fiber 103 for the light for collimation is conducted through the light emitting optical system 58 from the micro lens 62A to mirror 62B and then reflected by the special mirror 56 to come substantially on the optical axis 63. The laser light 218 for collimation is further conducted through the condensing optical system 57 and then emitted out of the laser light emission end $X_2$ so as to intermittently irradiate the object 200 to be surgically operated in the form of an light spot. The laser light for collimation partly reflected by the object 200 to be surgically operated is conducted to the light detectors 202 and 203 by means of the inner layer optical fibers 215 and the outer layer optical fibers 217 in accordance with the position of the object 200. In the same manner as explained in connection with FIG. 3 and FIG. 4, the proportion of the reflected light received by the inner layer optical fibers 215 and/or the outer layer optical fibers 217 will be determined depending on the position of the object 200 to be surgically operated. Processing of the signals and the control of the laser light for surgical operation after the light has been outputted from the light detectors 202 and 203 is the same as those already explained in connection with the prior art. When the position of the object 200 to be surgically operated to be irradiated by the laser light 218 for collimation is located nearer to the opening of the laser light emission end $X_2$ than a position included in the indefinite distance range $\Delta l_1$ already described with reference to FIG. 4, the oscillation tube part 211 for generating the laser for surgical operation is allowed to provide the laser light for surgical operation. This laser light for surgical operation is conducted by the infrared fiber 101 and emitted from the output end through a predetermined opening and transmitted through the special mirror 56. The laser light for surgical operation is conducted through the condensing optical system 57 comprising the condensing lens 107 and the condensing lens 108 and emitted outside of the laser light emission end $X_2$ to be condensed at the condensing point 64 on the optical axis 63. It is as a matter of course that the location of said condensing point 64 is nearer to the opening side of the laser light emission end $X_2$ than the position where the indefinite distance range $\Delta l_1$ is located. The laser light for surgical operation emitted from said laser light emission end $X_2$ irradiates the object 200 to be surgically operated in the form of a light spot and removes the object by burning it. When the position of the object 200 to be surgically operated to be irradiated by said laser light 218 for collimation is located within said indefinite distance range $\Delta l_1$, output of the laser light for surgical operation will be decided depending on the reflective condition of the surface of the object 200 to be surgically operated as explained earlier in connection with the prior art. Further when the position of the object 200 to be surgically operated to be irradiated by the laser light 218 for collimation is located farther from the opening of the laser light emission end $X_2$ than the position included in the indefinite distance range $\Delta l_1$, the laser light for surgical operation will not be provided by the oscillation tube part 211 for generating the laser light for surgical operation and accordingly the object 200 to be surgically operated will not be irradiated.

As explained above, according to the apparatus for preventing erroneous emission according to the present invention, the optical axes of the laser light for collimation and the laser light for surgical operation emitted from the laser light emission end $X_2$ are combined together, and even if the apparatus for preventing erroneous emission for a laser scalpel according to the prior art is applied to the laser scalpel of an infrared fiber type, the range in which determination of the position for justifying emission of the laser light for surgical operation will be uncertain may be equivalent to that of the conventional laser scalpel of a multi-articulation mirror manipulator type and thus problems may be eliminated in respect of practical application. It is to be noted that although embodiments without a metallic tube or metallic coating around the infrared fiber 101 have been described, a metallic tube or metallic coating may be applied around the infrared fiber 101 in the conventional manner. It is also to be noted that although the laser having an oscillation tube as the source for supplying the light for collimation has been used a light emitting diode or semi-conductor laser may be used instead. In this case, it is also possible to optically modulate the light source directly by electrical signals without using an optical chopper part.

Figure 18:
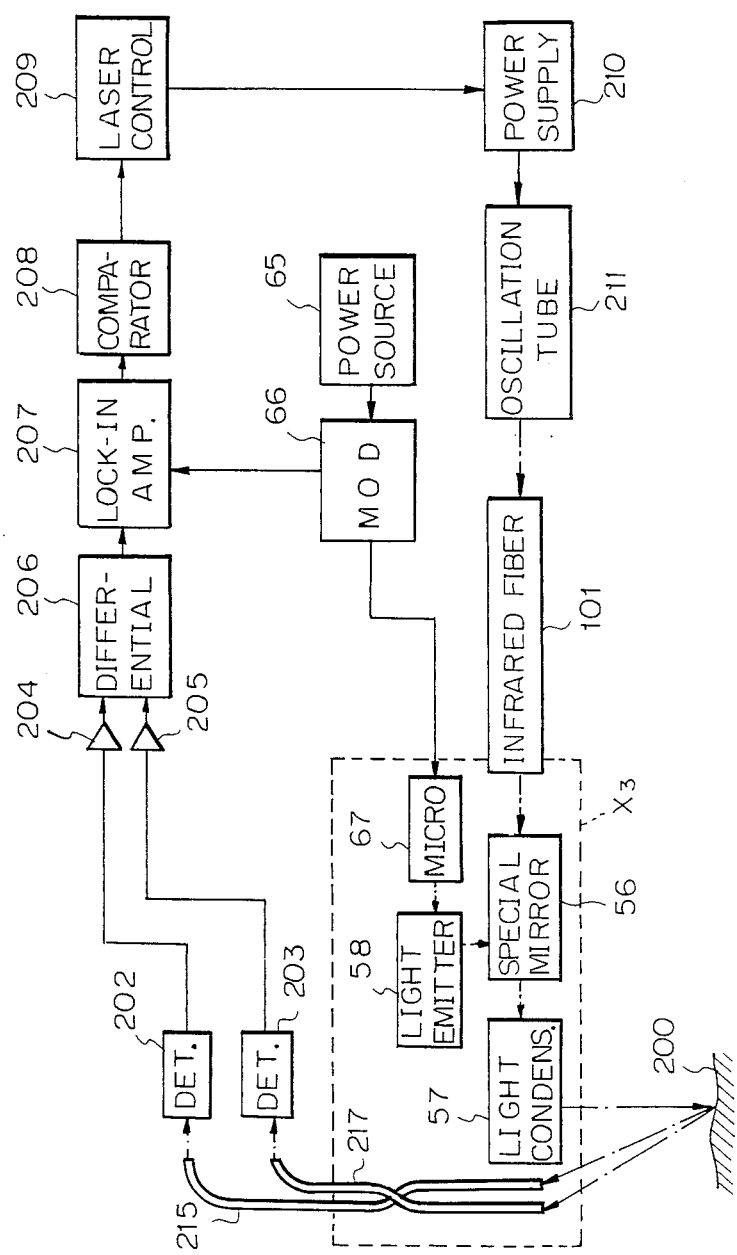
FIG. 18 is the block diagram showing the third embodiment of the apparatus for preventing erroneous emission for a laser scalpel of an optical fiber type according to the present invention.

FIG. 18 is an overall block diagram illustrating another embodiment of the present invention. In FIG. 18, numeral 65 designates the power source for the light for collimation; numeral 66 a modulating circuit adapted to modulate the output from said power source 65 and provide its output; and numeral 67 a micro light emitting source of a semi-conductor such as a semi-conductor laser or a light emitting diode which is electrically connected at the input side to the output side of the modulating circuit 66 by a lead wire 68. The output light provided by said micro light emitting source 67 of a semi-conductor is incident into the light emitting optical system 57 and the lock-in amplifier 207 receives the modulated signal from the modulating circuit 66. Sign $X_3$ designates the laser light emission end which comprises the special mirror 56, the light condensing optical system 57, the light emitting optical system 58, the micro light emitting source of a semi-conductor 67, the inner layer optical fibers 215, the outer layer optical fibers 217 and the tip end portion of the infrared fiber 101. Other constituting elements denoted with the same reference numbers as those of FIG. 16 are identical with those in the embodiment shown in FIG. 16 and the explanations thereof are not repeated here.

FIG. 19 illustrates in the vertical section the laser emission end $X_3$ according to the embodiment shown in FIG. 18. In FIG. 19, the micro light emitting source 67 of a semiconductor is disposed at the incidence side of the micro lens 62A and secured between the outer cylinder 59 and the inner cylinder 60. The construction of other constituting elements denoted with the same reference numbers as those in FIG. 17 are the same as those shown in FIG. 17 and the explanations thereof are not repeated. According to this embodiment, the output of the power source 65 is modulated by the modulating circuit 66 and thus the modulated signals are supplied to the micro light emitting source 67 of a semi-conductor by way of the lead wired 68 while the micro light emitting source 67 of a semi-conductor serves to emit the light for collimation to the micro lens 62A. According to this embodiment, unlike the embodiment shown in FIG. 16, the optical fiber 103 for the light for collimation are not used, thereby making the entire apparatus easy to handle and making it compact, for the light source is very tiny.

According to the present invention, in addition to the foregoing embodiments, an insertable mirror may be provided on the optical axes of the oscillation tube part 211 for generating the laser for operation and the infrared fiber 101 and the laser control part 209 is so construct as to be able to provide the signal enabling the actuator for inserting said mirror to be driven whereby said laser control part 209 may be able to control the output of the laser light for surgical operation without controlling the power source 210 for providing the laser light. It is also to be noted that when said mirror is inserted on the optical axis, the laser light for surgical operation to be reflected by said mirror may be arranged to irradiate the cooling pipe passing the cooling liquid therethrough or a non-reflective member of heat resistance property.

It is further to be understood that the inner layer optical fiber 215 and the outer layer optical fiber 217 for conducting the reflected light may be consisted of each single optical fiber. It is also possible to provide two annular light receiving elements at the input end in place of the light detectors 202 and 203 without using the inner layer optical fibers 215 and the outer layer optical fibers 217.

While there has been described preferred embodiments of the invention, obviously modifications and variations are possible in light of the above teachings. It is therefore to be understood that within the scope of the appended claims, the invention may be practiced otherwise than as specifically described.

What is claimed is:
1. An infrared fiber cable comprising:
an infrared fiber adapted to conduct and emit an invisible light;
a light emitting means disposed around said infrared fiber and adapted to emit a visible light for collimation;
a protective tube containing said infrared fiber therein for isolating said invisible light from said visible light; and
a member having spacedly disposed externally forward and rearward surfaces disposed in the path of invisible light and for allowing said invisible light to pass from the inside to the outside of said protective tube through said member, entering said rearward surface and exiting said forward surface thereof, and for allowing said visible light to be reflected from the external forward surface of said member, wherein said light emitting means includes mirror means disposed forward of said member so as to re-direct said visible light from a forwardly-directed path to a rearwardly-directed path for direction to the external forward surface of said member.

2. A cable as claimed in claim 1 wherein said member comprises a window member that closes an otherwise open end of said protective tube to thus provide isolation between said visible light and said invisible light.

3. A cable as claimed in claim 2 wherein said window member is constructed to transmit invisible light therethrough while only reflecting visible light directed to the external forward surface thereof without allowing visible light to be transmitted therethrough, so that both said visible and said invisible light are directed in the same direction.

4. A cable as claimed in claim 1 wherein said member is in the form of a plate and is disposed on the optical path of the infrared light beam perpendicular to the optical axis of said infrared light beam.

5. A cable as claimed in claim 1 wherein said member is in the form of a plate and is disposed on the optical path of the infrared light beam at an angle of inclination of 45 degrees relative to the axis of said infrared light beam emitted from said infrared fiber.

6. A cable as claimed in claim 1 wherein said member is a lens.

7. A cable as claimed in claim 1 wherein said light emitting means is an optical fiber adapted to shine the light output from a light emitting diode.

8. A cable as claimed in claim 1 wherein said mirror means is disposed outside the path of said invisible light.

9. An infrared fiber cable comprising:
an infrared fiber adapted to conduct and emit an infrared light beam and means for emitting a visible light for collimation,
the improvement comprising:
a protective tube provided to contain said infrared fiber therein to isolate said infrared light from said visible light;
a member having spacedly disposed external forward and rearward surfaces disposed in the path of invisible light to allow said infrared beam to pass from the inside to the outside of said protective tube through said member, entering said rearward surface exiting said forward surface thereof, and to allow said visible light to be reflected from the external forward surface of said member, and mirror means disposed forward of said member so as to re-direct visible light from a forwardly-directed path for direction to the external forward surface of said member, the visible light directed from the outside of said member being reflected from the external forward surface of said member, thereby enabling said infrared light and said visible light to be directed in the same direction.

10. A cable as claimed in claim 9 wherein said member comprises a window member that closes an otherwise open end of said protective tube to thus provide isolation between said visible light and said infrared light.

11. A cable as claimed in claim 10 wherein said window member is constructed to transmit infrared light therethrough while only reflecting visible light directed to the external forward surface thereof without allowing visible light to be transmitted therethrough, so that both said visible and said infrared light are directed in the same direction.

12. A cable as claimed in claim 9 wherein said member is in the form of a plate and is disposed on the optical path of said infrared light beam perpendicular to the optical axis of said infrared light beam emitted from said infrared fiber.

13. A cable as claimed in claim 9 wherein said member is in the form of a plate and is disposed on the optical path of said infrared light beam at an angle of inclination of 45 degrees relative to the optical axis of said infrared light beam emitted from said infrared fiber.

14. A cable as claimed in claim 9 wherein said member is a lens.

15. A cable as claimed in claim 9 wherein a light emitting diode is used as the source of light for collimation.

16. A cable as claimed in claim 9 wherein a laser diode is used as the source of light collimation.

17. A cable as claimed in claim 9 wherein said mirror means is disposed outside of the path of said infrared light beam.

* * * * *